United States Patent [19]

Teutsch et al.

[11] 4,233,296

[45] Nov. 11, 1980

[54] 11β-SUBSTITUTED-Δ$^{4,9}$-ESTRADIENES

[75] Inventors: Jean G. Teutsch, Le Blanc-Mesnil; Daniel Philibert, La Varenne Saint-Hilaire, both of France

[73] Assignee: Roussel Uclaf, Paris, France

[21] Appl. No.: 867,485

[22] Filed: Jan. 6, 1978

[30] Foreign Application Priority Data

Jan. 13, 1977 [FR] France ................................. 77 00858

[51] Int. Cl.$^2$ ..................... A61K 31/58; A61K 31/56; C07J 17/00; C07J 1/00

[52] U.S. Cl. ................................ 424/241; 260/239.5; 260/239.55 R; 260/397.3; 260/397.45; 424/242; 424/243

[58] Field of Search ....................... /Steroids MS File

[56] References Cited

U.S. PATENT DOCUMENTS 3,978,048  8/1976  Basco ............................ 260/239.55 R

FOREIGN PATENT DOCUMENTS 2429040  1/1975  Fed. Rep. of Germany ........ 260/397.1
2237906  2/1975  France ........................... 260/239.55 C

OTHER PUBLICATIONS

Bowers et al, Tetrahedron, vol. 7 (1959), pp. 153-162.

*Primary Examiner*—Ethel G. Love
*Attorney, Agent, or Firm*—Hammond & Littell

[57] ABSTRACT

Novel steroids of the formula

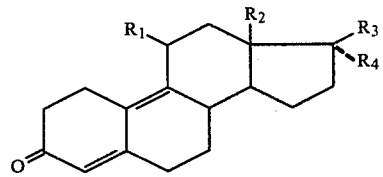

wherein $R_1$ is linear or branched alkyl of 1 to 12 carbon atoms, unsaturated alkyl of 2 to 8 carbon atoms optionally substituted, optionally substituted aryl of 6 to 12 carbon atoms, optionally substituted aralkyl of 7 to 13 carbon atoms and a heterocycle with at least one sulfur or oxygen atom, $R_2$ is alkyl of 1 to 4 carbon atoms, $R_3$ is selected from the group consisting of hydrogen, hydroxy, acyloxy of an organic carboxylic acid of 1 to 18 carbon atoms, alkoxy of 1 to 8 carbon atoms and acyl of an organic carboxylic acid of 1 to 18 carbon atoms and $R_4$ is selected from the group consisting of hydrogen, hydroxy, alkyl and alkoxy of 1 to 8 carbon atoms, alkenyl and alkynyl of 2 to 8 carbon atoms and acyloxy of an organic carboxylic acid of 1 to 18 carbon atoms, with the proviso that $R_4$ is not hydrogen when $R_1$ is allyl, $R_2$ is methyl and $R_3$ is hydroxy having progestomimetic properties and their preparation.

32 Claims, No Drawings

11β-SUBSTITUTED-Δ$^{4,9}$-ESTRADIENES

STATE OF THE ART

U.S. Pat. No. 3,325,520 describes certain 11β-alkyl steroids, but Δ$^4$-3-ones.

OBJECTS OF THE INVENTION

It is an object of the invention to provide the novel Δ$^{4,9}$-steroids of formula I and a novel process for their preparation.

It is another object of the invention to provide novel progestomimetic compositions and to a novel method of inducing progestomimetic activity in warm-blooded animals.

These and other objects and advantages of the invention will become obvious from the following detailed description.

THE INVENTION

The novel Δ$^{4,9}$-steroids of the invention have the formula

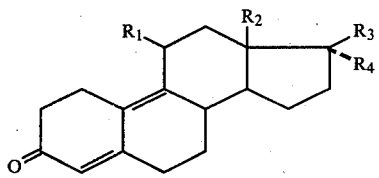

wherein $R_1$ is linear or branched alkyl of 1 to 12 carbon atoms, unsaturated alkyl of 2 to 8 carbon atoms optionally substituted, optionally substituted aryl of 6 to 12 carbon atoms, optionally substituted aralkyl of 7 to 13 carbon atoms and a heterocycle with at least one sulfur or oxygen atom, $R_2$ is alkyl of 1 to 4 carbon atoms, $R_3$ is selected from the group consisting of hydrogen, hydroxy, acyloxy of an organic carboxylic acid of 1 to 18 carbon atoms, alkoxy of 1 to 8 carbon atoms and acyl of an organic carboxylic acid of 1 to 18 carbon atoms and $R_4$ is selected from the group consisting of hydrogen, hydroxy, alkyl and alkoxy of 1 to 8 carbon atoms, alkenyl and alkynyl of 2 to 8 carbon atoms and acyloxy of an organic carboxylic acid of 1 to 18 carbon atoms, with the proviso that $R_4$ is not hydrogen when $R_1$ is allyl, $R_2$ is methyl and $R_3$ is hydroxy.

Examples of $R_1$ are alkyl such as methyl, ethyl, propyl, isopropyl, butyl, isobutyl, tert.-butyl, n-pentyl, n-hexyl, 2-methyl-pentyl, 2,3-dimethyl-butyl, n-heptyl, 2-methyl-hexyl, 2,2-dimethylpentyl, 3,3-dimethylpentyl, 3-ethylpentyl, n-octyl, 2,2-dimethylhexyl, 3,3-dimethylhexyl, 3-methyl-3-ethylpentyl, nonyl, 2,4-dimethylheptyl and n-decyl; unsaturated alkyl such as vinyl, isopropenyl, allyl, 2-methylallyl and isobutenyl; substituted unsaturated alkyl, preferably with a thioalkyl such as thiomethyl or thioethyl or one or more halogens such as fluorine atoms; aryyl and aralkyl such as phenyl or benzyl optionally substituted in the o-, m- or p-positions with at least one member of the group consisting of alkyl of 1 to 4 carbon atoms, alkoxy of 1 to 4 carbon atoms such as methoxy, halogens such as chlorine or fluorine and —CF$_3$; and heterocycles such as thienyl, isothienyl and furyl.

Examples of $R_2$ are alkyl such as methyl, ethyl and propyl. Examples of $R_3$ and $R_4$ are alkoxy such as methoxy, ethoxy, propoxy, isopropoxy, butoxy, isobutoxy and tert.-butoxy; acyl or acyloxy of an organic carboxylic acid of 1 to 18 carbon atoms such as alkanoic acids such as formic acid, acetic acid, propionic acid, butyric acid, isobutyric acid or undecylic acid; hydroxyalkanoic acids such as hydroxyacetic acid; cycloalkylcarboxylic acids and cycloalkylalkanoic acids such as cyclopropylcarboxylic acid, cyclobutylcarboxylic acid, cyclopentylcarboxylic acid, cyclohexylcarboxylic acid, cyclopentylacetic acid, cyclohexylacetic acid, cyclopentylpropionic acid or cyclohexylpropionic acid; benzoic acid; phenylalkanoic acids such as phenylacetic acid or phenylpropionic acid; or amino acids such as diethylaminoacetic acid or aspartic acid.

Further examples of $R_4$ are alkyl such as methyl, ethyl, propyl or butyl; alkenyl such as vinyl, allyl, 2-methylallyl or isobutenyl; and alkynyl such as ethynyl, 1-propynyl, 2-propynyl, 2-butynyl or butadiynyl.

Among the preferred compounds of formula I are those wherein $R_2$ is methyl or ethyl, those wherein $R_1$ is straight or branched chain alkyl of 1 to 12 carbon atoms, those wherein $R_1$ is branched or straight chain alkenyl or alkynyl of 2 to 4 carbon atoms optionally suubstituted with alkylthio of 1 to 4 carbon atoms or one or more fluorine atoms especially vinyl, those wherein $R_1$ is phenyl or benzyl optionally substituted on the phenyl with alkoxy of 1 to 4 carbon atoms, those wherein $R_1$ is thienyl, those wherein $R_4$ is hydrogen or ethynyl and those wherein $R_3$ is hydroxy, alkoxy of 1 to 8 carbon atoms and optionally substituted acyloxy of 1 to 18 carbon atoms

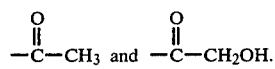

Specific preferred compounds of formula I are 11β-vinyl-17α-methyl-17β-acetyl-Δ$^{4,9}$-estradiene-3-one, 11β-vinyl-17α-acetoxy-17β-acetyl-Δ$^{4,9}$-estradiene-3-one and 11β-vinyl-17β-acetyl-Δ$^{4,9}$-estradiene-17β-ol-3-one.

The novel process of the invention for the preparation of compounds of formula I comprises reacting a compound of the formula

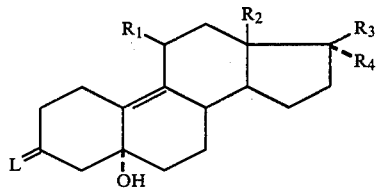

wherein $R_1$, $R_2$, $R_3$ and $R_4$ have the above definitions and L is a ketal group with a deshydration agent capable of freeing the corresponding ketone group to obtain the corresponding compound of formula I which may be esterified or etherified when there is a 17-OH group or saponified when there is a 17-acyloxy group.

Preferably, the deshydration agent is a sulfonic acid resin such as commercial sulfonic acid resins with a polystyrene or polystyrene/divinylbenzene base but equally useful are mineral acids such as hydrochloric acid or sulfuric acid in a lower alkanol or perchloric acid in acetic acid or a sulfonic acid such as p-toluene sulfonic acid.

The esterification agent is preferably a carboxylic acid in the presence of an acid catalyst and preferentially the water formed is eliminated. The saponification agent is preferably an alkali metal base such as sodium hydroxide or potassium hydroxide, potassium amide, potassium tert.-butylate or lithium acetylide in ethylenediamine and the saponification is preferably effected in a lower alkanol such as methanol or ethanol.

The compounds of formula II are novel products described and claimed in commonly assigned application Ser. No. 867,484 filed on even date herewith which are prepared by reacting a comound of the formula

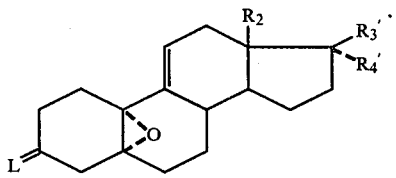

wherein $R_2$ and L have the above definition and either $R_3'$ is hydrogen, hydroxy, alkoxy of 1 to 8 carbon atoms, acyl or acyloxy of an organic carboxylic acid of 1 to 18 carbon atoms and $R_4'$ is hydrogen, hydroxy, alkyl or alkoxy of 1 to 8 carbon atoms, alkenyl or alkynyl of 2 to 8 carbon atoms, cyano or acyloxy of an organic carboxylic acid of 1 to 18 carbon atoms or $R_3'$ is a blocked hydroxy in the form of an easily removable ether and $R_4'$ is cyano or $R_3'$ is cyano and $R_4'$ is a blocked hydroxy in the form of an easily removable ether with a compound selected from the group consisting of $(R_1)_2CuLi$, $R_1MgHal$ or $R_1Li$ wherein $R_1$ has the above definition and Hal is a halogen, in the presence of a catalytic amount of a cuprous halide when $R_1 Mg Hal$ and $R_1Li$ are used.

The compounds of formula III are generally known compounds which may be prepared by the process of French Pat. No. 2,082,129, No. 1,550,974 or No. 2,201,287. Compounds of the formula

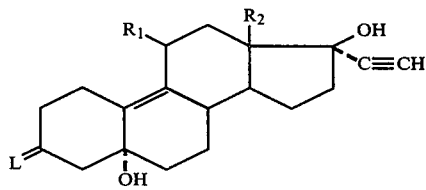

wherein L, $R_1$ and $R_2$ have the above definitions may be prepared by reacting a compound of the formula

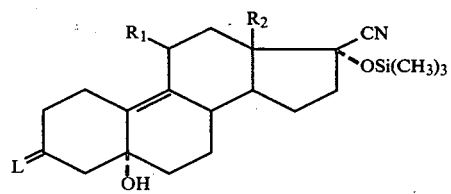

with a complex of lithium acetylide and ethylenediamine. Compounds of the formula

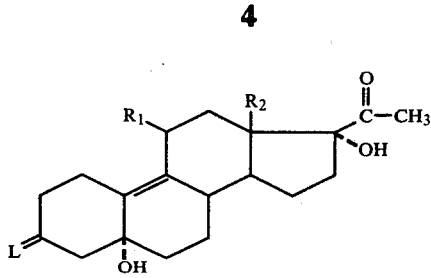

may be prepared by reacting a compound of the formula

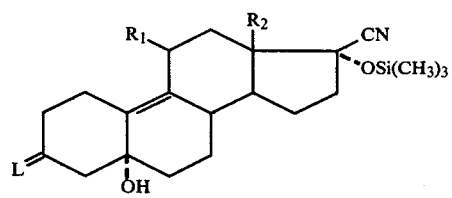

with a methyl magnesium halide such as the chloride, bromide or iodide. Compounds of the formula

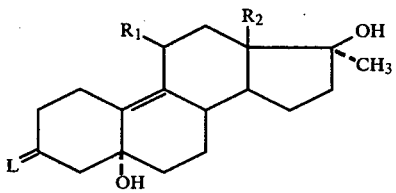

wherein $R_1$, $R_2$ and L have the above definitions may be prepared by reacting a compound of the formula

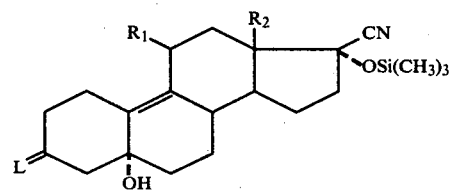

with a saponification agent to obtain a compound of the formula

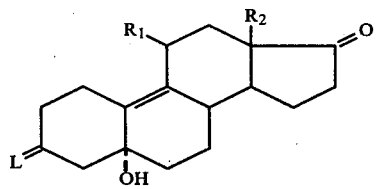

which is then reacted with a methyl magnesium halide.

The novel progestomimetic compositions of the invention are comprised of a progestomimetically effective amount of at least one compound of formula I and an inert pharmaceutical carrier or excipient. The compositions may be in the form of tablets, coated tablets, cachets, capsules, granules, emulsions, syrups, suppositories or injectable solutions or suspensions.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants or emulsifiers and preservatives.

The compositions due to their progestomimetic activity are useful for the treatment of amenorrhea, of hypermenorrhea, dysmenorrhea and of luteal insufficiency. Particularly active compounds of formula I are those having a 17α-ethynyl or acetoxy group and a 17β-hydroxy or acetyl group.

The compounds of formula I having a 17α-hydrogen or methyl and a 17β-hydroxy have an activity presented as an androgen antagonist and agonist component. These compositions are useful as antagonists in the treatment of hypertrophic (adenoma) and cancer of the prostrate, of hyperandrogenia, of acne, of hirsutism and for agonists in the treatment of andropause, of adiposogenital syndrome, of functional metrorragy, of fibroma and endometroiosis as well as for asthenia, osteoporsis, senescences and metabolic pertubations after prolonged corticotheraphy.

The preferred compositions of the invention are those containing 11β-vinyl-17α-methyl-17β-acetyl-$\Delta^{4,9}$-estradiene-3-one and 11β-vinyl-17α-acetoxy-17β-acetyl-$\Delta^{4,9}$-estradiene-3-one.

The novel method of the invention for inducing progestomimetic activity in warm-blooded animals, including humans, comprises administering to warm-blooded animals a progestomimetically effective amount of at least one compound of formula I. The compounds may be administered orally, rectally, transcutaneously or intravenously. The usual daily dose is 0.002 to 0.2 mg/kg depending on the compound and the method of administration.

In the following examples there are described several preferred embodiments to illustrate the invention. However, it is to be understood that the invention is not intended to be limited to the specific embodiments.

PREPARATION 1

3-[(1,2-ethanediyl)-acetal] of 11β-phenyl-17α-trimethylsilyloxy-17β-cyano-$\Delta^9$-estrene-5α-ol-3-one 5 mg of cuprous chloride were added to 1.1 ml of a solution of 1.17 M of phenyl magnesium bromide in tetrahydrofuran and after cooling the mixture to $-15°$ C. a solution of 430 mg of the 3-[(1,2-ethanediyl)-acetal] of 5α,10α-epoxy-17α-trimethylsilyloxy-17β-cyano-$\Delta^{9(11)}$-estrene-3-one in 2 ml of tetrahydrofuran was added thereto. The mixture was then stirred for 105 minutes at 0° C. and was then poured into an aqueous ammonium chloride solution. The mixture was extracted with ether and the ether extracts were dried and evaporated to dryness to obtain 503 mg of product which was crystallized from isopropyl ether to obtain 366 mg of the 3-[(1,2-ethanediyl)-acetal] of 11β-phenyl-17α-trimethylsilyloxy-17β-cyano-$\Delta^9$-estrene-5α-ol-3-one melting at 184° C.

PREPARATION 2

Using the procedure of preparation 1, propyl magnesium bromide and 3-[(1,2-ethanediyl)-acetal] of 5α,10α-epoxy-17α-trimethylsilyloxy-17β-cyano-$\Delta^{9(11)}$-estrene-3-one were reacted to obtain a 60% yield of 3-[(1,2-ethanediyl)-acetyl] of 11β-propyl-17α-trimethylsilyloxy-17β-cyano-$\Delta^9$-estrene-5α-ol-3-one with a specific rotation of $[\alpha]_D^{20} = -58.5° \pm 2.5°$ (c=0.5% in ethanol).

PREPARATION 3

Using the procedure of preparation 1, isopropyl magnesium bromide and 3-[(1,2-ethanediyl)-acetal] of 5α,10α-epoxy-17α-trimethylsilyloxy-17β-cyano-$\Delta^{9(11)}$-estrene-3-one were reacted to obtain an 86% yield of 3-[(1,2-ethanediyl)-acetal] of 11β-isopropyl-17α-trimethylsilyloxy-17β-cyano-$\Delta^9$-estrene-5α-ol-3-one with a specific rotation of $[\alpha]_D^{20} = -70° \pm 3°$ (c=0.5% in CHCl$_3$).

PREPARATION 4

Using the procedure of preparation 1, decyl magnesium bromide and 3-[(1,2-ethanediyl)-acetal] of 5α,10α-epoxy-17α-trimethylsilyloxy-17β-cyano-$\Delta^{9(11)}$-estrene-3-one were reacted to obtain a 92% yield of 3-[(1,2-ethanediyl)-acetal] of 11β-decyl-17α-trimethylsilyloxy-17β-cyano-$\Delta^9$-estrene-5α-ol-3-one with a specific rotation of $[\alpha]_D^{20} = -42° \pm 1.5°$ (c=0.7% in CHCl$_3$).

PREPARATION 5

Using the procedure of preparation 1, vinyl magnesium bromide and 3-[(1,2-ethanediyl)-acetal] of 5α,10α-epoxy-17α-trimethylsilyloxy-17β-cyano-$\Delta^{9(11)}$-estrene-3-one were reacted to obtain 88% yield of 3-[(1,2-ethanediyl)-acetal] of 11β-vinyl-17α-trimethylsilyloxy-17β-cyano-$\Delta^9$-estrene-5α-ol-3-one with a melting point of 213° C. and a specific rotation of $[\alpha]_D^{20} = -60° \pm 2°$ (c=0.85% in CHCl$_3$)

PREPARATION 6

Using the procedure of preparation 1, isopropenyl magnesium bromide and 3-[(1,2-ethanediyl)-acetal] of 5α,10α-epoxy-17α-trimethylsilyloxy-17β-cyano-$\Delta^{9(11)}$-estrene-3-one were reacted to obtain a 78% yield of 3-[(1,2-ethanediyl)-acetal] of 11β-isopropenyl-17α-trimethylsilyloxy-17β-cyano-$\Delta^9$-estrene-5α-ol-3-one with a melting point of 136° C. and a specific rotation of $[\alpha]_D^{20} = -58° \pm 2.5°$ (c=0.4% in CHCl$_3$).

PREPARATION 7

Using the procedure of preparation 1, p-methoxyphenyl magnesium bromide and 3-[(1,2-ethanediyl)-acetal] of 5α,10α-epoxy-17α-trimethylsilyloxy-17β-cyano-$\Delta^{9(11)}$-estrene-3-one were reacted to obtain a 92% yield of 3-[(1,2-ethanediyl)-acetal] of 11β-p-methoxyphenyl-17α-trimethylsilyloxy-17β-cyano-$\Delta^9$-estrene-5α-ol-3-one melting at 210° C. and having a specific rotation of $[\alpha]_D^{20} = -12° + 2°$ (c=0.4% in CHCl$_3$).

PREPARATION 8

Using the procedure of preparation 1, benzyl magnesium bromide and 3-[(1,2-ethanediyl)-acetal] of 5α,10α-epoxy-17α-trimethylsilyloxy-17β-cyano-$\Delta^{9(11)}$-estrene-3-one were reacted to obtain a 94% yield of 3-[(1,2-ethanediyl)-acetal] of 11β-benzyl-17α-trimethylsilyloxy-17β-cyano-$\Delta^9$-estrene-5α-ol-3-one melting at 160° C. and having a specific rotation of $[\alpha]_D^{20} = -86° \pm 3°$ (c=0.3% in CHCl$_3$)

PREPARATION 9

Using the procedure of preparation 1, 2-thienyl magnesium bromide and 3-[(1,2-ethanediyl)-acetal] of 5α,10α-epoxy-17α-trimethylsilyloxy-17β-cyano-$\Delta^{9(11)}$-estrene-3-one were reacted to obtain a 92% yield of 3-[(1,2-ethanediyl)-acetal] of 11β-(2-thienyl)-17α-trimethylsilyloxy-17β-cyano-$\Delta^9$-estrene-5α-ol-3-one with a melting point of 260° C. and a specific rotation of $[\alpha]_D^{20} = +34° \pm 2.5°$ (c=0.4% in CHCl$_3$).

PREPARATION 10

4.6 ml of a 2.2 M solution of methyllithium in ethyl ether were added at 0° C. to a suspension of 955 mg of cuprous iodide in 5 ml of ether and then 436 mg of 3-[(1,2-ethanediyl)-acetal] of 5α,10α-epoxy-17β-benzyloxy-Δ$^{9(11)}$-estrene-3-one and 2 ml of tetrahydrofuran were added thereto. The mixture was stirred at 0° C. for 35 minutes and was then poured into an aqueous ammonium chloride solution. The mixture was extracted with ether and the ether extracts were dried and evaporated to dryness under reduced pressure to obtain 460 mg of 3-[(1,2-ethanediyl)-acetal] of 11β-methyl-17β-benzoyloxy-Δ$^9$-estrene-5α-ol-3-one.

RMN Spectrum (60 MHz): 18 CH, 67 Hz; 11-CH; 63-71 Hz; 11-H, 180 Hz.

PREPARATION 11

Using the procedure of preparation 10, lithium diethyl cuprate was reacted with 3-[(1,2-ethanediyl)-acetal] of 5α,10α-epoxy-17α-trimethylsilyloxy-17β-cyano-Δ$^{9(11)}$-estrene-3-one to obtain a 100% yield of 3-[(1,2-ethanediyl)-acetal] of 11β-ethyl-17α-trimethylsilyloxy-17β-cyano-Δ$^9$-estrene-5α-ol-3-one with a specific rotation of $8\alpha]_D^{20} = -61° \pm 2.5°$ (c=0.5% in CHCl$_3$).

PREPARATION 12

Using the procedure of preparation 10, lithium diphenyl cuprate was reacted with 3-[(1,2-ethanediyl)-acetal] of 5α,10α-epoxy-17α-trimethylsilyloxy-17β-cyano-Δ$^{9(11)}$-estrene-3-one to obtain a 98.6% yield of 3-[(1,2-ethanediyl)-acetal] of 11β-phenyl-17α-trimethylsilyloxy-17β-cyano-Δ$^9$-estrene-5α-ol-3-one with a melting point of 186° C. and a specific rotation of $[\alpha]_D^{20} = -12.5° \pm 2°$ (c=0.6% in CHCl$_3$).

PREPARATION 13

Using the procedure of preparation 10, lithium diphenyl cuprate was reacted with 3-[(1,2-ethanediyl)-acetal] of 5α,10α-epoxy-17β-benzoyloxy-Δ$^{9(11)}$-estrene-3-one to obtain a 70% yield of 3-[(1,2-ethanediyl)-acetal] of 11β-phenyl-17β-benzoyloxy-Δ$^9$-estrene-5α-ol-3-one melting at 188° C. and having a specific rotation of $[\alpha]_D^{20} = +12° \pm 2°$ (c=0.45% in CHCl$_3$).

PREPARATION 14

6 ml of t-butyllithium were added at −50° C. to a suspension of 0.81 g of a dimethylsulfide-cuprous bromide complex in 5 ml of tetrahydrofuran and then 10 ml of tetrahydrofuran were added thereto. After 15 minutes, a solution of 0.840 g of 3-[(1,2-ethanediyl)-acetal] of 5α,10α-epoxy-17α-trimethylsilyloxy-17β-cyano-Δ$^{9(11)}$-estrene-3-one in 10 ml of tetrahydrofuran was added thereto and the mixture was stirred at −25° C. for 16 hours and was then poured into an aqueous ammonium chloride solution. The mixture was extracted with ether and the ether extracts were dried and evaporated to dryness to obtain 0.942 g of 3-[(1,2-ethanediyl)-acetal] of 11β-t-butyl-17α-trimethylsilyloxy-17β-cyano-Δ$^9$-estrene-5α-ol-3-one with a specific rotation of $[\alpha]_D^{20} = -58° \pm 3°$ (c=0.3% in CHCl$_3$).

PREPARATION 15

16 ml of a solution of 0.88 M of tert.-butyllithium in tetrahydrofuran were added at −70° C. to a solution of 1.8 g of methoxyethylene in 10 ml of tetrahydrofuran and the mixture was held at −10° C. for 30 minutes to obtain a solution of methoxy vinyllithium. The said solution was added at −40° C. to suspension of 1.4 g of dimethylsulfide-cuprous bromide complex in 5 ml of tetrahydrofuran and a solution of 1.3 g of 3-[(1,2-ethanediyl)-acetal] of 5α,10α-epoxy-17α-trimethylsilyloxy-17β-cyano-Δ$^{9(11)}$-estrene-3-one in 5 ml of tetrahydrofuran was added thereto. The mixture was held at −10° C. for 90 minutes and was then poured into an aqueous ammonium chloride solution. The mixture was extracted with ether and the ether extracts were dried and evaporated to dryness to obtain 1.3 g of 3-[(1,2-ethanediyl)-acetal] of 11β-methoxy-vinyl 17α-trimethylsilyloxy-17β-cyano-Δ$^9$-estrene-5α-ol-3-one with a specific rotation of $[\alpha]_D^{20} = -56° \pm 2°$ (c=0.4% in CHCl$_3$).

PREPARATION 16

A solution of 26.8 g of allyl phenyl ether in 75 ml of ether at −15° C. was added to a suspension of 5.6 g of lithium in 150 ml of tetrahydrofuran to obtain a solution of allyllithium. 83 ml of the said solution were added at −78° C. to a suspension of 5.15 g of a dimethylsulfide-cuprous bromide complex in 20 ml of tetrahydrofuran and after 15 minutes at −70° C., a solution of 4.13 g of 3-[(1,2-ethanediyl)-acetal] of 5α,10α-epoxy-17α-trimethylsilyloxy-17β-cyano-Δ$^{9(11)}$-estrene-3-one in 20 ml of tetrahydrofuran was added thereto. After 30 minutes, the mixture was poured into an aqueous ammonium chloride solution which was then extracted with ether. The ether extracts were dried and evaporated to dryness to obtain 4.2 g of 3-[(1,2-ethanediyl)-acetal] of 11β-allyl-17α-trimethylsilyloxy-17β-cyano-Δ$^9$-estrene-5α-ol-3-one with a specific rotation of $[\alpha]_D^{20} = -52° \pm 2°$ (c=0.6% in CHCl$_3$).

PREPARATION 17

Using the procedure of preparation 1, o-methoxyphenyl magnesium bromide was reacted with the acetal to obtain an 86% yield of 3-[(1,2-ethanediyl)-acetal] of 11β-o-methoxyphenyl-17α-trimethylsilyloxy-17β-cyano-Δ$^9$-estrene-5α-ol-3-one with a specific rotation of $[\alpha]_D^{20} = -16.5° \pm 1°$ (c=0.55% in CHCl$_3$).

PREPARATION 18

Using the procedure of preparation 1, p-fluorophenyl magnesium bromide was reacted with the ecetal to obtain a 90% yield of 3-[(1,2-ethanediyl)-acetal] of 11β-p-fluorophenyl-17α-trimethylsilyloxy-17β-cyano-Δ$^9$-estrene-5α-ol-3-one with a melting point of 166° C. and a specific rotation of $[\alpha]_D^{20} = -7.5° \pm 2°$ (c=0.5% in CHCl$_3$).

PREPARATION 19

A few drops of pyridine and 22 ml of a solution of 0.75 M of hexafluoroacetone hydroperoxide were added at 0° C. to a solution of 4.68 g of 3-[(1,2-ethanediyl)-acetal] of 18-methyl-Δ$^{5(10),9(11)}$-estradiene-17β-ol-3-one (by process of Belgium Pat. No. 632,347) in 200 ml of methylene chloride and the mixture was stirred for 30 minutes and was poured into an aqueous sodium thiosulfate-sodium bicarbonate solution. The mixture was extracted with ether and the ether extracts were evaporated to dryness to obtain 2 g of 3-[1,2-ethanediyl)-acetal] of 5α,10α-epoxy-18-methyl-Δ$^{9(11)}$-estrene-17β-ol-3-one.

Using the procedure of preparation 1, 1.5 g of the above acetal and 16 ml of a solution of vinyl magnesium bromide (13.6 mm) in tetrahydrofuran were reacted to obtain 0.98 g of 3-[(1,2-ethanediyl)-acetal] of 11β-vinyl-18-methyl-$\Delta^9$-estrene-5α-17β-diol-3-one.

PREPARATION 20

14 ml of a solution of 0.43 M of ethyllithium in ether were added at −20° C. to a suspension of 570 mg of cuprous iodide in ether and then 872 mg of 3-[(1,2-ethanediyl)-acetal] of 5α,10α-epoxy-17β-benzoyloxy-$\Delta^{9(11)}$-estrene-3-one were added thereto. The temperature was allowed to rise to 0° C. and the mixture was poured into an aqueous ammonium chloride solution. The mixture was extracted with ether and the ether extracts were dried and evaporated to dryness under reduced pressure to obtain 966 mg of 3-[(1,2-ethanediyl)-acetal] of 11β-ethyl-17β-benzoyloxy-$\Delta^9$-estrene-5α-ol-3-one.

diamine and the mixture was stirred for 19 hours at room temperature after which another 2 g of the complex were added thereto. The mixture was then stirred at room temperature for one hour, at 45° C. for 105 minutes and then at room temperature for 15 hours after which another 1 g of the complex was added. The mixture was heated at 45° C. for 1 hour and after addition of 1 g of the complex, the mixture was heated at 40° C. for 30 minutes. The mixture was poured into ice water and was extracted with ether. The ether extracts were dried and evaporated to dryness to obtain 3-[(1,2-ethanediyl)-acetyl] of 11β-ethyl 17α-ethylnyl-$\Delta^9$-estrene-5α,17β-diol-3-one which was used as is.

PREPARATIONS 22 to 33

Using the procedure of preparation 21, the starting materials of Table I were reacted to obtain the final products listed therein.

TABLE I

| STARTING PRODUCT | FINAL PRODUCT |
|---|---|
| 3-[(1,2-ethanediyl)-acetal] of 11β-propyl-17β-cyano-17α-trimethyl-silyloxy-$\Delta^9$-estrene-5α-ol-3-one | 3-[(1,2-ethanediyl)-acetal] of 11β-propyl-17α-ethynyl-$\Delta^9$-estrene-5α,17β-diol-3-one melting at 170° C. |
| 3-[(1,2-ethanediyl)-acetal] of 11β-isopropyl-17β-cyano-17α-trimethylsilyloxy-$\Delta^9$estrene-5α-ol-3-one | 3-[(1,2-ethanediyl)-acetal] of 11β-isopropyl-17α-ethynyl-$\Delta^9$-estrene-5α,17β-diol-3-one melting at 175° C. |
| 3-[(1,2-ethanediyl)-acetal] of 11β-decyl-17β-cyano-17α-trimethylsilyloxy-$\Delta^9$-estrene-5α-ol-3-one | 3-[(1,2-ethanediyl-acetal] of 11β-decyl-17α-ethynyl-$\Delta^9$-estrene-5α,17β-diol-3-one with an Rf = 0.27 (petroleum ether-ethyl acetate 6-4) |
| 3-[(1,2-ethanediyl)-acetal] of 11β-vinyl-17β-cyano-17α-trimethylsilyloxy-$\Delta^9$-estrene-5α-ol-3-one | 3-[(1,2-ethanediyl)-acetal] of 11β-vinyl-17α-ethynyl-$\Delta^9$-estrene-5α,17β-diol-3-one melting at 160° C. |
| 3-[(1,2-ethanediyl)-acetal] of 11β-isopropenyl-17β-cyano-17α-trimethylsilyloxy-$\Delta^9$-estrene-5α-ol-3-one | 3-[(1,2-ethanediyl)-acetal] of 11β-isopropenyl-17α-ethynyl-$\Delta^9$-estrene-5α,17β-diol-3-one melting at 193° C. |
| 3-[(1,2-ethanediyl)-acetal] of 11β-allyl-17β-cyano-17α-trimethylsilyloxy-$\Delta^9$-estrene-5α-ol-3-one | 3-[(1,2-ethanediyl)-acetal] of 11β-allyl-17α-ethynyl-$\Delta^9$-estrene-5α,17β-diol-3-one |
| 3-[(1,2-ethanediyl)acetal]of 11β-benzyl-17β-cyano-17α-trimethylsilyloxy-$\Delta^9$-estrene-5α-ol-3-one | 3-[(1,2-ethanediyl)-acetal] of 11β-benzyl-17α-ethynyl-$\Delta^9$-estrene-5α,17β-diol-3-one melting at 152° C. |
| 3-[(1,2-ethanediyl)-acetal] of 11β- (p-methoxyphenyl)-17β-cyano-17α-trimethylsilyloxy-$\Delta^9$-estrene-5α-ol-3-one | 3-[(1,2-ethanediyl)-acetal] of 11β-(p-methoxyphenyl)-17α-ethynyl-$\Delta^9$-estrene-5α,17β-diol-3-one melting at 150° C. |
| 3-[(1,2-ethanediyl)-acetal] of 11β-(2-thienyl)-17β-cyano-17α-trimethylsilyloxy-$\Delta^9$-estrene-5α-ol-3-one | 3-[(1,2-ethanediyl)-acetal] of 11β-(2-thienyl)-17α-ethynyl-$\Delta^9$-estrene-5α,17β-diol-3-one melting at 140° C. |
| 3-[(1,2-ethanediyl)-acetal] of 11β-(o-methoxyphenyl)-17β-cyano-17α-trimethylsilyloxy-$\Delta^9$-estrene-5α-ol-3-one | 3-[(1,2-ethanediyl)-acetal] of 11β-(o-methoxyphenyl)-17α-ethynyl-$\Delta^9$-estrene-5α,17β-diol-3-one |
| 3-[(1,2-ethanediyl)-acetal] of 11β-(p-fluorophenyl)-17β-cyano-17α-trimethylsilyloxy-$\Delta^9$-estrene-5α-ol-3-one | 3-[(1,2-ethanediyl)-acetal] of 11β-(p-fluorophenyl)-17α-ethynyl-$\Delta^9$-estrene-5α,17β-diol-3-one |
| 3-[(1,2-ethanediyl)-acetal] of 11β-phenyl-17β-cyano-17α-trimethylsilyloxy-$\Delta^9$-estrene-5α-ol-3-one | 3-[(1,2-ethanediyl)-acetal] of 11β-phenyl-17α-ethynyl-$\Delta^9$-estrene-5α,17β-diol-3-one |

PREPARATION 21

2 mg of a complex of lithium acetylide-ethylenediamine were added to a solution of 2.3 g of 3-[(1,2-ethanediyl)-acetal] of 11β-ethyl-17α-trimethylsilyloxy-17β-cyano-$\Delta^9$-estrene-5α-ol-3-one in 50 ml of ethylene

PREPARATION 34

1 g of 3-[(1,2-ethanediyl)-acetal] of 11β-ethyl-17β-cyano-17α-trimethylsilyloxy-6$6^9$-estrene-5α-ol-3-one was added to 8.8 ml of a solution of 0.98 M of methyl magnesium bromide in tetrahydrofuran and the mixture was refluxed for 19 hours and was then poured into an aqueous ammonium chloride solution. The mixture was extracted with methylene chloride and the organic extracts were dried and evaporated to dryness to obtain 904 mg of 3-[(1,2-ethanediyl)-acetal] of 11β-ethyl-17β-acetyl-Δ$^9$-estrene-5α,17β-diol-3-one melting at 166°–168° C.

PREPARATION 35

7 ml of 0.98 M of methyl magnesium bromide in tetrahydrofuran were concentrated by distilling off 3.9 ml of tetrahydrofuran and then 240 mg of 3-[(1,2-ethanediyl)-acetal] of 11β-phenyl-17β-cyano-17α-trimethylsilyloxy-Δ$^9$-estrene-5α-ol-3-one were added thereto. The mixture was refluxed for 5½ hours and was then poured into an aqueous ammonium chloride solution. The mixture was extracted with methylene chloride and the organic extracts were dried and evaporated to dryness to obtain 252 mg of 3-[(1,2-ethanediyl)-acetal] of 11β-phenyl-17β-acetyl-Δ$^9$-estrene-5α,17β-diol-3-one melting at 159°–162° C.

PREPARATION 36

10 g of 3-[(1,2-ethanediyl)-acetal] of 17α-methyl-17β-acetyl-Δ$^{5(10),9(11)}$-estradiene-3-one [process of French Pat. No. 2,149,302] were added to a solution of 0.5 ml of pyridine in 240 ml of methylene chloride and after cooling the mixture to 0° C., 40 ml of a solution of 30 mm of hexafluoroacetone were added thereto. After 10 minutes, the mixture was poured into an aqueous sodium bicarbonate-sodium theiosulfate solution and the mixture was extracted with methylene chloride. The organic extracts were dried and evaporated to dryness and the residue was crystallized from isopropyl ether to obtain 8.2 g of 3-[(1,2-ethanediyl)-acetal] of 5α,10α-epoxy-17α-methyl-17β-acetyl-Δ$^{9(11)}$-estrene-3-one.

PREPARATION 37

150 mg of cuprous chloride were added at −40° C. to a 17.6 ml of a solution of vinyl magnesium bromide in tetrahydrofuran and then a solution of 4 g of the above acetal in 15 ml of tetrahydrofuran was added thereto. After standing at −40° C. for 2 hours, the mixture was poured into an aqueous ammonium chloride solution. The mixture was extracted with ether and the extracts were dried and evaporated to dryness. The residue was crystallized from isopropyl ether to obtain 2.68 g of 3-[(1,2-ethanediyl)-acetal] of 11β-vinyl-17α-methyl-17β-acetyl-Δ$^9$-estrene-5α-ol-3-one.

PREPARATION 38

1.4 g of 3-[(1,2-ethanediyl)-acetal] of 11β-vinyl-17β-cyano-17α-trimethylsilyloxy-Δ$^9$-estrene-5α-ol-3-one were added to 16 ml of a 2 M solution of methyl magnesium bromide in tetrahydrofuran and the mixture was refluxed for 17 hours and was poured into an aqueous ammonium chloride solution. The mixture was extracted with ether and the ether extracts were evaporated to dryness to obtain 3-[(1,2-ethanediyl)-acetal] of 11β-vinyl-17β-acetyl-Δ$^9$-estrene-5α,17β-diol-3-one.

PREPARATION 39

30 mg of cuprous chloride were added at −70° C. to 3 ml of a solution of 1.45 M of methyllithium in ether and after stirring the mixture for 15 minutes, a solution of 0.86 g of 3-[(1,2-ethanediyl)-acetal] of 5α,10α-epoxy-17α-trimethyl-silyloxy-17β-cyano-Δ$^{9(11)}$-estrene-3-one in 5 ml of tetrahydrofuran was added thereto. The mixture was stirred at −70° C. for 30 minutes and then at −30° C. for one hour and at 10° C. for 2 hours. The mixture was poured into an aqueous ammonium chloride solution and the mixture was extracted with ether. The ether extracts were dried and evaporated to dryness and the residue was chromatographed over silica gel. Elution with a 7–3 benzene-ethyl acetate mixture yielded 3-[(1,2-ethanediyl)-acetal] of 11β-methyl-17α-trimethylsilyloxy-17β-cyano-Δ$^9$-estrene-5α-ol-3-one melting at 165° C. and having a specific rotation of $[\alpha]_D^{20} = -54° \pm 2.5°$ (c=0.5% of CHCl$_3$).

RMN Spectrum (CDCl$_3$): 18-CH$_3$-64 Hz; 11-CH$_3$-64 to 71.5 Hz; 11-H-192 Hz; ketal-240 Hz; —OH— 257 Hz; —SiMe$_3$—12.5 Hz.

PREPARATION 40

5 ml of sodium hydroxide were added to a solution of 1.5 g of 3-[(1,2-ethanediyl)-acetal] of 11β-propyl-17α-trimethylsilyloxy-17β-cyano-Δ$^9$-estrene-5α-ol-3-one in 50 ml of ethanol and the mixture was stirred for 30 minutes at 20° C. and was then poured into water. The mixture was extracted with ether and the ether extracts were dried and evaporated to dryness. The residue was taken up in 5 ml of tetrahydrofuran and 30 ml of a solution of 1 M methyl magnesium bromide in tetrahydrofuran was added thereto. The mixture was refluxed for 8 hours and was then concentrated. The temperature was held at 20° C. for 15 hours and the mixture was poured into aqueous ammonium chloride solution. The mixture was extracted with ether and the ether extracts were dried and evaporated to dryness. The residue was treated a second time with magnesium as above to obtain 1.3 g of 3-[(1,2-ethanediyl)-acetal] of 11β-propyl-17α-methyl-Δ$^9$-estrene-5α,17β-diol-3-one.

PREPARATION 41 to 48

Using the procedure of preparation 40, the acetals of Table II were reacted to obtain the final products listed therein.

TABLE II

| STARTING ACETAL | FINAL PRODUCT |
|---|---|
| 3-[(1,2-ethanediyl)-acetal] of 11β-isopropyl-17α-trimethyl-silyloxy-17β-cyano-Δ$^9$-estrene-5α-ol-3-one | 3-[(1,2-ethanediyl)-acetal] of 11β-isopropyl-17α-methyl-Δ$^9$-estrene-5α,17β-diol-3-one |
| 3-[(1,2-ethanediyl)-acetal] of 11β-decyl-17α-trimethylsily-loxy-17β-cyano-Δ$^9$-estrene-5α-ol-3-one | 3-[(1,2-ethanediyl)-acetal] of 11β-decyl-17α-methyl-Δ$^9$-estrene-5α,17β-diol-3-one. |
| 3-[(1,2-ethanediyl)-acetal] of 11β-isopropenyl-17α-trimethyl-silyloxy-17β-cyano-Δ$^9$-estrene-5α-ol-3-one | 3-[(1,2-ethanediyl)-acetal] of 11β-isopropenyl-17α-methyl-Δ$^9$-estrene-5α,17β-diol-3-one |
| 3-[(1,2-ethanediyl)-acetal] of | 3-[(1,2-ethanediyl)-acetal] of |

TABLE II-continued

| STARTING ACETAL | FINAL PRODUCT |
| --- | --- |
| 11β-allyl-17α-trimethylsily-loxy-17β-cyano-Δ⁹-estrene-5α-ol-3-one | 11β-allyl-17α-methyl-Δ⁹-estrene-5α,17β-diol-3-one |
| 3-[(1,2-ethanediyl)-acetal] of 11β-vinyl-17α-trimethylsilyloxy-17β-cyano-Δ⁹-estrene-5α-ol-3-one | 3-[(1,2-ethanediyl)-acetal] of 11β-vinyl-17α-methyl-Δ⁹-estrene-5α,17β-diol-3-one |
| 3-[(1,2-ethanediyl)-acetal] of 11β-(p-methoxyphenyl)-17α-trimethylsilyloxy-17β-cyano-Δ⁹-estrene-5α-ol-3-one | 3-[(1,2-ethanediyl)-acetal] of 11β-(p-methoxyphenyl)-17α-methyl-Δ⁹-estrene-5α,17β-diol-3-one |
| 3-[(1,2-ethanediyl)-acetal] of 11β-benzyl-17α-trimethylsily-loxy-17β-cyano-Δ⁹-estrene-5α-ol-3-one | 3-[(1,2-ethanediyl)-acetal] of 11β-benzyl-17α-methyl-Δ⁹-estrene-5α,17β-diol-3-one |
| 3-[(1,2-ethanediyl)-acetal] of 11β-(2-thienyl)-17α-trimethylsilyloxyl-17β-cyano-Δ⁹-estrene-5α-ol-3-one | 3-[(1,2-ethanediyl)-acetal] of 11β-(2-thienyl)-17α-methyl-Δ⁹-estrene-5α,17β-diol-3-one. |

EXAMPLE 1

11β-methyl-17β-benzoyloxy-Δ⁴,⁹-estradiene-3-one 400 mg of Redex CF resin were added to a mixture of 905 mg of 3-[(1,2-ethanediyl)-acetal] of 11β-methyl-Δ⁹-estrene-5α,17β-diol-3-one in 6 ml of 95% ethanol and the mixture was refluxed for one hour. The mixture was vacuum filtered and one part of the filtrate was evaporated to dryness. The residue was taken up in methylene chloride and the organic phase was washed with aqueous sodium chloride and dried and evaporated to dryness. The residue was crystallized from isopropyl ether to obtain 640 mg of 11β-methyl-17β-benzoyloxy-Δ⁴,⁹-estradiene-3-one melting at 134° C.

EXAMPLE 2

11β-ethyl-Δ⁴,⁹-estradiene-17β-ol-3-one

A mixture of 966 mg of 3-[(1,2-ethanediyl)-acetal] of 11β-ethyl-Δ⁹-estrene-5α,17β-diol-3-one, 1 ml of sodium hydroxide solution, 15 ml of 95% ethanol and 1 ml of water was stirred at 20° C. for 4 hours and was then acidified and extracted with methylene chloride. The organic extracts were treated with Redex CF (a sulfonic acid resin) in 95% ethanol by refluxing for 30 minutes. The mixture was vacuum filtered and the filtrate was evaporated to dryness. The residue was taken up in methylene chloride and the organic phase was washed with water, dried and evaporated to dryness. The residue was chromatographed over silica gel and was eluted with a 9-1 chloroform-ethyl acetate mixture to obtain 440 mg of 11β-ethyl-Δ⁴,⁹-estradiene-17β-ol-3-one with a specific rotation of $[\alpha]_D^{20} = +127° \pm 3°$ (c=0.6% in chloroform).

EXAMPLE 3

11β-phenyl-17β-benzoyloxy-Δ⁴,⁹-estradiene-3-one

Using the procedure of Example 1, 168 mg of 3-[(1,2-ethanediyl)-acetal] of 11β-phenyl-17β-benzoyloxy-Δ⁹-estrene-5α-ol-3-one were reacted to obtain 144 mg of 11β-phenyl-17β-benzoyloxy-Δ⁴,⁹-estradiene-3-one melting towards 140° C. and having a specific rotation of $[\alpha]_D^{20} = +139.5° \pm 3.5°$ (c=0.5% in chloroform).

EXAMPLE 4

11β-phenyl-Δ⁴,⁹-estradiene-17β-ol-3-one 0.3 ml of sodium hydroxide solution was added to a solution of 125 mg of the product of Example 3 in 3 ml of 45% aqueous ethanol and the mixture was stirred for one hour and was then poured into a 1 N hydrochloric acid solution. The mixture was extracted with chloroform and the organic extracts were evaporated to dryness to obtain 45 mg of 11β-phenyl-Δ⁴,⁹-estradiene-17β-ol-3-one with a specific rotation of $[\alpha]_D^{20} = +144° \pm 3°$ (c=0.75% in chloroform).

EXAMPLE 5

Using the procedure of Example 1, 3-[(1,2-ethanediyl)-acetal] of 11β-ethyl-17α-ethynyl-Δ⁹-estrene-5α,17β-diol-3-one was reacted to obtain 11β-ethyl-17α-ethynyl-Δ⁴,⁹-estradiene-17β-ol-3-one melting at 177° C. and having a specific rotation of $[\alpha]_D^{20} = -202° \pm 4°$ (c=0.47% in CHCl₃).

EXAMPLE 6

Using the procedure of Example 1, 3-[(1,2-ethanediyl)-acetal] of 11β-propyl-17α-ethynyl-Δ⁹-estrene-5α,17β-diol-3-one was reacted to obtain 11β-propyl-17α-ethynyl-Δ⁴,⁹-estradiene-17β-ol-3-one melting at 185° C. and having a specific rotation of $[\alpha]_D^{20} = -151.5° \pm 3.5°$ (c=0.5% in CHCl₃).

EXAMPLE 7

Using the procedure of Example 1, 3-[(1,2-ethanediyl)-acetal] of 11β-isopropyl-17α-ethynyl-Δ⁹-estrene-5α,17β-diol-3-one was reacted to obtain 11β-isopropyl-17α-ethynyl-Δ⁴,⁹-estradiene-17β-ol-3-one melting at 178° C. and having a specific rotation of $[\alpha]_D^{20} = -165.5° \pm 4°$ (c=0.4% in CHCl₃).

EXAMPLE 8

Using the procedure of Example 1, 3-[(1,2-ethanediyl)-acetal] of 11β-decyl-17α-ethynyl-Δ⁹-estrene-5α,17β-diol-3-one was reacted to obtain 11β-decyl-17α-ethynyl-Δ⁴,⁹-estradiene-17β-ol-3-one with a specific rotation of $[\alpha]_D^{20} = -103° \pm 3°$ (c=0.5% in CHCl₃).

EXAMPLE 9

11β-vinyl-17α-ethynyl-Δ⁴,⁹-estradiene-17β-ol-3-one

A mixture of 2.85 g of 3-[(1,2-ethanediyl)-acetal] of 11β-vinyl-17α-ethynyl-Δ⁹-estrene-5α,17β-diol-3-one, 3 g of Redex CF resin and 200 ml of 95% ethanol was refluxed for 30 minutes and was then filtered. The filtrate was evaporated to dryness and the residue was chromatographed over silica gel. Elution with a 6-4 petroleum ether-ethyl acetate mixture yielded 2.02 g of 11β-vinyl-17α-ethynyl-Δ$^{4,9}$-estradiene-17β-ol-3-one melting at 125° C.

EXAMPLE 10

11β-vinyl-17α-ethynyl-17β-acetoxy-Δ$^{4,9}$-estradiene-3-one

A solution of 1.25 g of the product of Example 9, 18 ml of acetic acid, 3.75 ml of trifluoroacetic acid anhydride and 150 mg of p-toluene sulfonic acid was stirred for one hour at room temperature and was then poured into water. The mixture was extracted with ether and the ether extracts were evaporated to dryness. The residue was chromatographed over silica gel and was eluted with a 7–3 benzene-ethyl acetate mixture to obtain 0.702 g of 11β-vinyl-17α-ethynyl-17β-acetoxy-Δ$^{4,9}$-estradiene-3-one with a specific rotation of $[\alpha]_D^{20} = -81° \pm 3°$ (c=0.25% in chloroform).

EXAMPLES 11 to 16

Using the procedure of Example 9, the acetals of Table III were reacted to obtain the Δ$^{4,9}$-estradienes of Table III.

TABLE III

| STARTING PRODUCTS | FINAL PRODUCTS |
| --- | --- |
| 3-[(1,2-ethanediyl)-acetal] of 11β-isopropenyl-17α-ethynyl-Δ$^9$-estrene-5α,17β-diol-3-one | 11β-isopropenyl-17α-ethynyl-Δ$^{4,9}$-estradiene-17β-ol-3-one melting at 190° C. |
| 3-[(1,2-ethanediyl)-acetal] of 11β-allyl-17α-ethynyl-Δ$^9$-estrene-5α,17β-diol-3-one | 11β-allyl-17α-ethynyl-Δ$^{4,9}$-estradiene-17β-ol-3-one melting at 167° C. |
| 3-[(1,2-ethanediyl)-acetal] of 11β-benzyl-17α-ethynyl-Δ$^9$-estrene-5α,17β-diol-3-one | 11β-benzyl-17α-ethynyl-Δ$^{4,9}$-estradiene-17β-ol-3-one melting at 179° C. |
| 3-[(1,2-ethanediyl)-acetal] of 11β-p-methoxyphenyl-17α-ethynyl-Δ$^9$-estrene-5α,17β-diol-3-one | 11β-(p-methoxyphenyl)-17α-ethynyl-Δ$^{4,9}$-estradiene-17β-ol-3-one melting at 200° C. |
| 3-[(1,2-ethanediyl)-acetal] of 11β-(2-thienyl)-17α-ethynyl-Δ$^9$-estrene-5α,17β-diol-3-one | 11β-(2-thienyl)-17α-ethynyl-Δ$^{4,9}$-estradiene-17β-ol-3-one melting at 209° C. |
| 3-[(1,2-ethanediyl)-acetal] of 11β-(o-methoxyphenyl)-17α-ethynyl-Δ$^9$-estrene-5α,17β-diol-3-one | 11β-(o-methoxyphenyl)-17α-ethynyl-Δ$^{4,9}$-estradiene-17β-ol-3-one melting at 235° C. |

EXAMPLES 17 to 21

Using the procedure of Example 1, the acetals of Table IV were reacted to form the Δ$^{4,9}$-estradienes of Table IV.

TABLE IV

| STARTING PRODUCT | FINAL PRODUCT |
| --- | --- |
| 3-[(1,2-ethanediyl)-acetal] of 11β-ethyl-17β-acetyl-Δ$^9$-estrene-5α,17α-diol-3-one | 11β-ethyl-17β-acetyl-Δ$^{4,9}$-estradiene-17α-ol-3-one melting at 180°–181° C. and having a specific rotation of $[\alpha]_D^{20} = -140.5 + 3°$ (c = 0.5% in CHCl$_3$) |
| 3-[(1,2-ethanediyl)-acetal] of 11β-phenyl-17β-acetyl-Δ$^9$-estrene-5α,17α-diol-3-one | 11β-phenyl-17β-acetyl-Δ$^{4,9}$-estradiene-17α-ol-3-one melting at 270° C. and having a specific rotation of $[\alpha]_D^{20} = +83.5 \pm 1°$ (c = 1% in CHCl$_3$) |
| 3-[(1,2-ethanediyl)-acetal] of 11β-vinyl-17α-methyl-17β-acetyl-Δ$^9$-estrene-5α-ol-3-one | 11β-vinyl-17α-methyl-17β-acetyl-Δ$^{4,9}$-estradiene-3-one-melting at 105° C. and having a specific rotation of $[\alpha]_D^{20} = -44 \pm 2°$ (c = 0.5% in CHCl$_3$) |
| 3-[(1,2-ethanediyl)-acetal] of 11β-vinyl-17β-acetyl-Δ$^9$-estrene-5α,17α-diol-3-one | 11β-vinyl-17β-acetyl-Δ$^{4,9}$-estradiene-17α-ol-3-one |
| 3-[(1,2-ethanediyl)-acetal] of 11β-vinyl-18-methyl-Δ$^9$-estrene-5α,17β-diol-3-one | 11β-vinyl-18-methyl-Δ$^{4,9}$-estradiene-17β-ol-3-one with a specific rotation of $[\alpha]_D^{20} = -43 \pm 2.5°$ (c = 0.5% in CHCl$_3$) |

EXAMPLE 22

11β-ethyl-17α-acetoxy-17β-acetyl-Δ$^{4,9}$-estradiene-3-one 0.2 ml of trifluoroacetic anhydride was added to a mixture of 67 mg of 11β-ethyl-17β-acetyl-Δ$^{4,9}$-estradiene-17α-ol-3-one in 1 ml of acetic acid and the mixture was stirred at room temperature for 105 minutes. Then, 0.3 ml of trifluoroacetic anhydride and 10 mg of p-toluene sulfonic acid were added thereto and the mixture was stirred for 35 minutes and was then poured into ice. The mixture was extracted with methylene chloride and the organic extracts were washed with aqueous sodium bicarbonate, dried and evaporated to dryness. The residue was chromatographed over silica gel and eluted with a 6-4 petroleum ether-ethyl acetate mixture to obtain 32 mg of 11β-ethyl-17α-acetoxy-17β-acetyl-Δ$^{4,9}$-estradiene-3-one melting at 158° C.

EXAMPLE 23

11β-vinyl-17α-acetoxy-17β-acetyl:Δ$^{4,9}$-estradiene-3-one

Using the procedure of Example 22, 11β-vinyl-17β-acetyl-Δ$^{4,9}$-estradiene-17α-ol-3-one was reacted to obtain 11β-vinyl-17α-acetoxy-17β-acetyl-Δ$^{4,9}$-estradiene-3-one with a specific rotation of $[\alpha]_D^{20} = +58° \pm 2.5°$ (c=0.5% in CHCl$_3$).

EXAMPLE 24

11β-propyl-17α-methyl-Δ$^{4,9}$-estradiene-17β-ol-3-one 1.6 g of Redex CF resin were added to a solution of 1.3 g of 3-[(1,2-ethanediyl)-acetal] of 11β-propyl-17α-methyl-Δ$^{4,9}$-estradiene-5α,17β-diol-3-one in 60 ml of 95% ethanol and the mixture was refluxed for one hour and was filtered. The filtrate was evaporated to dryness and the residue was chromatographed over silica gel. Elution with a 1-1 petroleum ether-ethyl acetate mixture yielded b 0.37 g of 11β-propyl-17α-methyl-Δ$^{4,9}$- estradiene-17β-ol-3-one with a specific rotation of [α]$_D^{20}$ = −114±5° (c=0.3% in CHCl$_3$).

EXAMPLES 25 TO 34

Using the procedure of Example 24, the acetals of Table V were reacted to obtain the Δ$^{4,9}$-estradienes of Table V.

TABLE V

| STARTING PRODUCTS | FINAL PRODUCTS |
|---|---|
| 3-[(1,2-ethanediyl)-acetal] of 11β-isopropyl-17α-methyl-Δ$^9$-estrene-5α,17β-diol-3-one | 11β-isopropyl-17α-methyl-Δ$^{4,9}$-estradiene-17β-ol-3-one with a specific rotation of [α]$_D^{20}$ = −166 ± 5° (c = 0.4% in CHCl$_3$) |
| 3-[(1,2-ethanediyl)-acetal] of 11β-decyl-17α-methyl-Δ$^9$-estrene-5β,17β-diol-3-one | 11β-decyl-17α-methyl-Δ$^{4,9}$-estradiene-17β-ol-3-one with a specific rotation of [α]$_D^{20}$ = −67.5 ± 2.5° (c = 0.5% in CHCl$_3$). |
| 3-[(1,2-ethanediyl)-acetal] of 11β-isopropenyl-17α-methyl-Δ$^9$-estrene-5α,17β-diol-3-one | 11β-isopropenyl-17α-methyl-Δ$^{4,9}$-estradiene-17β-ol-3-one melting at 144° C. and having a specific rotation of [α]$_D^{20}$ = −79.5 ± 2° (c = 0.9% in CHCl$_3$) |
| 3-[(1,2-ethanediyl)-acetal] of 11β-allyl-17α-methyl-Δ$^9$-estrene-5α,17β-diol-3-one | 11β-allyl-17α-methyl-Δ$^{4,9}$-estradiene-17β-ol-3-one with a specific rotation of [α]$_D^{20}$ = −103 ± 3° (c = 0.3% in CHCl$_3$) |
| 3-[(1,2-ethanediyl)-acetal] of 11β-vinyl-17α-methyl-Δ$^9$-estrene-5α,17β-diol-3-one | 11β-vinyl-17α-methyl-Δ$^{4,9}$-estradiene-17β-ol-3-one with a specific rotation of [α]$_D^{20}$ = −55 ± 2.5° (c = 0.5% in CHCl$_3$) |
| 3-[(1,2-ethanediyl)-acetal] of 11β-(p-methoxyphenyl)-17α-methyl-Δ$^9$-estrene-5α,17β-diol-3-one | 11β-(p-methoxyphenyl)-17α-methyl-Δ$^{4,9}$-estradiene-17β-ol-3-one melting at 131° C. and having a specific rotation of [α]$_D^{20}$ = −169 ± 5° (c = 0.3% in CHCl$_3$) |
| 3-[(1,2-ethanediyl)-acetal] of 11β-benzyl-17α-methyl-Δ$^9$-estrene-5α,17β-diol-3-one | 11β-benzyl-17α-methyl-Δ$^{4,9}$-estradiene-17β-ol-3-one melting at 158° C. and with a specific rotation of [α]$_D^{20}$ = +62 ± 2.5° (c = 0.6% in CHCl$_3$). |
| 3-[(1,2-ethanediyl-acetal] of 11β-(2-thienyl)-17α-methyl-Δ$^9$-estrene-5α,17β-diol-3-one | 11β-(2-thienyl)-17α-methyl-Δ$^{4,9}$-estradiene-17β-ol-3-one melting at 142° C. and with a specific rotation of [α]$_D^{20}$ = +140 ± 2.5° (c = 0.9% in CHCl$_3$) |
| 3-[(1,2-ethanediyl)-acetal] of 11β-(p-fluorophenyl)-17α-ethynyl-Δ$^9$-estrene-5α,17β-diol-3-one | 11β-(p-fluorophenyl)-17α-ethynyl-Δ$^{4,9}$-estradiene-17β-ol-3-one-melting at 222° C. and with a specific rotation of [α]$_D^{20}$ = + 53.5° ± 2 (c = 0.6% in CHCl$_3$). |
| 3-[(1,2-ethanediyl)-acetal] of 11β-phenyl-17α-ethynyl-Δ$^9$-estrene-5α,17β-diol-3-one | 11β-phenyl-17α-ethynyl-Δ$^{4,9}$-estradiene-17β-ol-3-one with a specific rotation of [α]$_D^{20}$ = + 47.5° ± 2° (c = 0.45% in CHCl$_3$) |

EXAMPLE 35

Tablets were prepared consisting of 0.5 mg of either 11β-vinyl-17α-methyl-17β-acetyl-Δ$^{4,9}$-estradiene-3-one or 11β-vinyl-17α-acetoxy-17β-acetyl-Δ$^{4,9}$-estradiene-3-one and sufficient excipient of talc, lactose, starch and magnesium stearate.

PHARMACOLOGICAL DATA

A. Progestomimetic Activity

The progestomimetic activity was determined for 11β-vinyl-17α-methyl-17β-acetyl-Δ$^{4,9}$-estradiene-3-one [product A], 11β-vinyl-17α-acetoxy-17β-acetyl-Δ$^{4,9}$-estradiene-3-one [product B] and 11β-vinyl-17α-ethynyl-Δ$^{4,9}$-estradiene-17α-ol-3-one [product C] was determined by the hormonal receptor method of Raynaud et al [J. Ster. Biochem., Vol. 6 (1975), p-615–622 and Physiology and Genetics of Reproduction, part A (1975), p. 143–160]. Immature rabbits received subcutaneously 25γ of estradiol and 5 days later, the animals were sacrificed and the uterus was removed and homogenized in a buffered solution of 10 mm of tromethamine, 0.25 M of saccharose and a pH of 7.4 with hydrochloric acid. The homogenate was centrifuged at 105,000 g per hour and the surnageant or cytosol was adjusted to a dilution of 1/50 (weight/volume). The resulting solution was incubated at 0° C. for 2 hours in tubes with the same volume of cytosol with a fixed concentration of tritiated 17,21-dimethyl-19-nor-Δ$^{4,9}$-pregnadiene-3,20-dione (designated as tritiated Product R) in the presence or not of an increasing concentration of radio-inactive 17,21-dimethyl-19-nor-$\Delta^{4,9}$-pregnadiene-3,20-dione (designated as cold product R) or progesterone or the test product. The radioactivity of the tritiated product R was determined after 2 hours by the technique of adsorption on carbon-dextran (1.25–0.625%). The curves representing the percentage of tritiated product R as a function of the log of the concentration, of cold product R, of progesterone or the test products and the $I_{50}$ straight line parallel to the axis of the abcisses and ordinates were plotted.

$$\frac{B}{T} = \frac{B/T \text{ Max.} + B/T \text{ Min.}}{2}$$

B/T max. is the percentage of tied tritiated product R when the product is not added and B/T min. is the percentage of tied tritiated product R when the maximum amount of cold product R is added. The intersections of these $I_{50}$ straight lines and the curves permit the determination of the values: CP - concentration of cold progesterone which inhibits by 50% the fixation of the tritiated product R and CX-concentration of test product which inhibits by 50% the fixation of tritiated product R. The relative affinity of the test product (ARL) was determined by the formula $$ARL = 100 \times \frac{CP}{CX}$$

and the results are reported in Table VI.

TABLE VI

| Product | ARL |
| --- | --- |
| Progesterone | 100 |
| A | 160 |
| B | 120 |
| C | 150 |

The results of Table VI show that products A, B and C have a greater affinity for specific uterine reception of progesterone than progesterone which means the products have progestomimetic activity.

B. Androgenic Activity

This test also used the method of Raynaud et al discussed above. The prostate was recovered from male rats castrated 24 hours earlier and was homogenized in a buffer containing 10 mm of tromethamine and 0.25 M of saccharose and sufficient hydrochloric acid for a pH of 7.4. The homogenate was centrifuged at 105,000 g for one hour and the surnageant liquid or cytosol was adjusted to a dilution of 1/5 (weight/volume). The liquid was incubated at 0° C. for 2 hours with a fixed concentration of tritiated 17α-methyl-$\Delta^{4,9,11}$-estratriene-17β-ol-3-one (tritiated product R) in the presence or absence of increasing concentrations of the same cold product (designated as cold product R), testosterone or the test compound.

The radioactivity of the tied tritiated product was determined after 2 hours by absorption technique on carbon-dextran (1.25%–0.625%). The curves representing the percentage of tied tritiated product R as a function of the log of the concentration, of the cold product R, testosterone or the test product added and the $I_{50}$ straight line parallel to the axis of the abcisses and ordinates.

$$\frac{B}{T} = \frac{B/T \text{ Max.} + B/T \text{ Min.}}{2}$$

were ploted. B/T max. is the percentage of tied tritiated product R when the product is not added and B/T min. is the percentage of tied tritiated product R when the maximum amount of cold product R is added. The intersections of these $I_{50}$ straight lines and the curves permit the determination of the values: CT-concentration of cold testosterone which inhibits by 50% the fixation of the tritiated product R and CX-concentration of test product which inhibits by 50% the fixation of tritiated product R. The relative affinity of the test product (ARL) was determined by the formula $$ARL = 100 \times \frac{CT}{CX}$$

and the results are reported in Table VII.

TABLE VII

| Product | ARL |
| --- | --- |
| Testosterone | 100 |
| Product D 11β-isopropenyl-17α-methyl-$\Delta^{4,9}$-estradiene-17β-ol-3-one | 80 |

The results of Table VII show that product D has an affinity on the order of that of testosterone for prostatic androgenic reception of testosterone and is therefore an androgen.

Various modifications of the products and process of the invention may be made without departing from the spirit or scope thereof and it is to be understood that the invention is intended to be limited only as defined in the appended claims.

We claim:

1. A compound of the formula

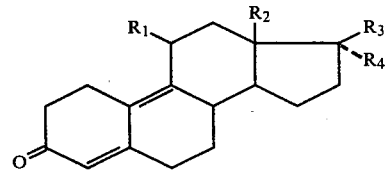

wherein $R_1$ is linear or branched alkyl of 1 to 12 carbon atoms, unsaturated alkyl of 2 to 8 carbon atoms optionally substituted with a member selected from the group consisting of alkylthio of 1 to 4 carbon atoms and halogens aryl of 6 to 12 carbon atoms and aralkyl of 7 to 13 carbon atoms optionally substituted with at least one member of the group consisting of alkyl and alkoxy of 1 to 4 carbon atoms, halogen and —$CF_3$ and a heterocycle selected from the group consisting of thienyl, isothienyl and furyl, $R_2$ is alkyl of 1 to 4 carbon atoms, $R_3$ is selected from the group consisting of hydrogen, hydroxy, acyloxy of an organic carboxylic acid of 1 to 18 carbon atoms, alkoxy of 1 to 8 carbon atoms and acyl of an organic carboxylic acid of 1 to 18 carbon atoms and $R_4$ is selected from the group consisting of hydrogen, hydroxy, alkyl and alkoxy of 1 to 8 carbon atoms, alkenyl and alkynyl of 2 to 8 carbon atoms and acyloxy of an organic carboxylic acid of 1 to 18 carbon atoms, with the proviso that $R_4$ is not hydrogen when $R_1$ is allyl, $R_2$ is methyl and $R_3$ is hydroxy.

2. A compound of claim 1 wherein $R_2$ is methyl.
3. A compound of claim 1 wherein $R_2$ is ethyl.
4. A compound of claim 1 wherein $R_1$ is alkyl of 1 to 12 carbon atoms.
5. A compound of claim 1 wherein $R_1$ is alkenyl or alkynyl of 2 to 4 carbon atoms optionally substituted with thioalkyl of 1 to 4 carbon atoms or fluorine.
6. A compound of claim 1 wherein $R_1$ is vinyl.
7. A compound of claim 1 wherein $R_1$ is phenyl or benzyl optionally substituted on the phenyl ring with alkoxy of 1 to 4 carbon atoms.
8. A compound of claim 1 wherein $R_1$ is thienyl.
9. A compound of claim 1 wherein $R_4$ is hydrogen.
10. A compound of claim 1 wherein $R_3$ is selected from the group consisting of hydroxy, alkoxy of 1 to 8 carbon atoms and acyloxy of an organic carboxylic acid of 1 to 18 carbon atoms.
11. A compound of claim 1 wherein $R_4$ is ethynyl.
12. A compound of claim 1 wherein $R_3$ is

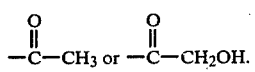

13. A compound of claim 1 selected from the group consisting of 11β-methyl-17β-benzoyloxy-Δ$^{4,9}$-estradiene-3-one, 11β-ethyl-Δ$^{4,9}$-estradiene-17β-ol-3-one, 11β-phenyl-17β-benzoyloxy-Δ$^{4,9}$-estradiene-3-one, 11β-phenyl-Δ$^{4,9}$-estradiene-17β-ol-3-one, 11β-ethyl-17α-ethynyl-Δ$^{4,9}$-estradiene-17β-ol-3-one, 11β-propyl-17α-ethynyl-Δ$^{4,9}$-estradiene-17β-ol-3-one, 11β-isopropyl-17α-ethynyl-Δ$^{4,9}$-estradiene-17β-ol-3-one, 11β-decyl-17α-ethynyl-Δ$^{4,9}$-estradiene-17β-ol-3-one, 11β-vinyl-17α-ethynyl-Δ$^{4,9}$-estradiene-17β-ol-3-one, 11β-vinyl-17α-ethynyl-17β-acetoxy-Δ$^{4,9}$-estradiene-3-one, 11β-isopropenyl-17α-ethynyl-Δ$^{4,9}$-estradiene-17β-ol-3-one, 11β-allyl-17α-ethynyl-Δ$^{4,9}$-estradiene-17β-ol-3-one, 11β-benzyl-17α-ethynyl-Δ$^{4,9}$-estradiene-17β-ol-3-one, 11β-(p-methoxyphenyl)-17α-ethynyl-Δ$^{4,9}$-estradiene-17β-ol-3-one, 11β-(2-thienyl)-17α-ethynyl-Δ$^{4,9}$-estradiene-17β-ol-3-one, 11β-(o-methoxyphenyl)-17α-ethynyl-Δ$^{4,9}$-estradiene-17β-ol-3-one, 11β-ethyl-17β-acetyl-Δ$^{4,9}$-estradiene-17α-ol-3-one, 11β-ethyl-17α-acetoxy-17β-acetyl-Δ$^{4,9}$-estradiene-3-one, 11β-phenyl-17β-acetyl-Δ$^{4,9}$-estradiene-17α-ol-3-one, 11β-vinyl-17α-methyl-17β-acetyl-Δ$^{4,9}$-estradiene-3-one, 11β-vinyl-17β-acetyl-Δ$^{4,9}$-estradiene-17α-ol-3-one, 11β-vinyl-17α-acetoxy-17β-acetyl-Δ$^{4,9}$-estradiene-3-one, 11β-vinyl-18-methyl-Δ$^{4,9}$-estradiene-17β-ol-3-one, 11β-propyl-17α-methyl-Δ$^{4,9}$-estradiene-17β-ol-3-one, 11β-isopropyl-17α-methyl-Δ$^{4,9}$-estradiene-17β-ol-3-one, 11β-decyl-17α-methyl-Δ$^{4,9}$-estradiene-17β-ol-3-one, 11β-isopropenyl-17α-methyl-Δ$^{4,9}$-estradiene-17β-ol-3-one, 11β-allyl-17β-allyl-17α-methyl-Δ$^{4,9}$-estradiene-17β-ol-3-one, 11β-vinyl-17α-methyl-Δ$^{4,9}$-estradiene-17β-ol-3-one, 11β-(p-methoxyphenyl)-17α-methyl-Δ$^{4,9}$-estradiene-17β-ol-3-one, 11β-benzyl-17α-methyl-Δ$^{4,9}$-estradiene-17β-ol-3-one and 11β-(2-thienyl)-17α-methyl-Δ$^{4,9}$-estradiene-17β-ol-3-one.

14. A compound of claim 1 selected from the group consisting of 11β-(p-fluorophenyl)-17α-ethynyl-Δ$^{4,9}$-estradiene-17β-ol-3-one and 11β-phenyl-17α-ethynyl-Δ$^{4,9}$-estradiene-17β-ol-3-one.

15. A progestomimetic composition comprising a progestomimetically effective amount of at least one compound of claim 1 and an inert pharmaceutical carrier.

16. A composition of claim 15 wherein $R_2$ is methyl.
17. A composition of claim 15 wherein $R_2$ is ethyl.
18. A composition of claim 15 wherein $R_1$ is alkyl of 1 to 12 carbon atoms.
19. A composition of claim 15 wherein $R_1$ is alkenyl or alkynyl of 2 to 4 carbon atoms optionally substituted with thioalkyl of 1 to 4 alkyl carbon atoms or fluorine.
20. A composition of claim 15 wherein $R_1$ is vinyl.
21. A composition of claim 15 wherein $R_1$ is phenyl or benzyl optionally substituted on the phenyl ring with alkoxy of 1 to 4 carbon atoms.
22. A composition of claim 15 wherein $R_1$ is thienyl.
23. A composition of claim 15 wherein $R_4$ is hydrogen.
24. A composition of claim 15 wherein $R_3$ is selected from the group consisting of hydroxy, alkoxy of 1 to 8 carbon atoms and acyloxy of an organic carboxylic acid of 1 to 18 carbon atoms.
25. A composition of claim 15 wherein $R_4$ is ethynyl.
26. A composition of claim 15 wherein $R_3$ is

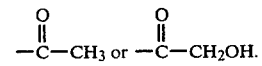

27. A composition of claim 15 when the compound is selected from the group consisting of 11β-methyl-17β-benzoyloxy-Δ$^{4,9}$-estradiene-3-one, 11β-ethyl-Δ$^{4,9}$-estradiene-17β-ol-3-one, 11β-phenyl-17β-benzoyloxy-Δ$^{4,9}$-estradiene-3-one, 11β-phenyl-Δ$^{4,9}$-estradiene-17β-ol-3-one, 11β-ethyl-17α-ethynyl-Δ$^{4,9}$-estradiene-17β-ol-3-one, 11β-propyl-17α-ethynyl-Δ$^{4,9}$-estradiene-17β-ol-3-one, 11β-isopropyl-17α-ethynyl-Δ$^{4,9}$-estradiene-17β-ol-3-one, 11β-decyl-17α-ethynyl-Δ$^{4,9}$-estradiene-17β-ol-3-one, 11β-vinyl-17α-ethynyl-Δ$^{4,9}$-estradiene-17β-ol-3-one, 11β-vinyl-17β-ethynyl-17β-acetoxy-Δ$^{4,9}$-estradiene-3-one, 11β-isopropenyl-17α-ethynyl-Δ$^{4,9}$-estradiene-17β-ol-3-one, 11β-allyl-17α-ethynyl-Δ$^{4,9}$-estradiene-17β-ol-3-one, 11β-benzyl-17β-benzyl-17α-ethynyl-Δ$^{4,9}$-estradiene-17β-ol-3-one, 11β-(p-methoxyphenyl)-17α-ethynyl-Δ$^{4,9}$-estradiene-17β-ol-3-one, 11β-(2-thienyl)-17α-ethynyl-Δ$^{4,9}$-estradiene-17β-ol-3-one, 11β-(o-methoxyphenyl)-17α-ethynyl-Δ$^{4,9}$-estradiene-17β-ol-3-one, 11β-ethyl-17β-acetyl-Δ$^{4,9}$-estradiene-17α-ol-3-one, 11β-ethyl-17α-acetoxy-17β-acetyl-Δ$^{4,9}$-estradiene-3-one, 11β-phenyl-17β-acetyl-Δ$^{4,9}$-estradiene-17α-ol-3-one, 11β-vinyl-17α-methyl-17β-acetyl-Δ$^{4,9}$-estradiene-3-one, 11β-vinyl-17β-acetyl-Δ$^{4,9}$-estradiene-17α-ol-3-one, 11β-vinyl-17α-acetoxy-17β-acetyl-Δ$^{4,9}$-estradiene-3-one, 11β-vinyl-18-methyl-Δ$^{4,9}$-estradiene-17β-ol-3-one, 11β-propyl-17α-methyl-Δ$^{4,9}$-estradiene-17β-ol-3-one, 11β-isopropyl-17α-methyl-Δ$^{4,9}$-estradiene-17β-ol-3-one, 11β-decyl-17α-methyl-Δ$^{4,9}$-estratiene-17β-ol-3-one, 11β-isopropenyl-17α-methyl-Δ$^{4,9}$-estradiene-17β-ol-3-one, 11β-allyl-17α-methyl-Δ$^{4,9}$-estradiene-17β-ol-3-one, 11β-vinyl-17α-methyl-Δ$^{4,9}$-estradiene-17β-ol-3-one, 11β-(p-methoxyphenyl)-17α-methyl-Δ$^{4,9}$-estradiene-17β-ol-3-one, 11β-benzyl-17α-methyl-Δ$^{4,9}$-estradiene-17β-ol-3-one and 11β-(2-thienyl)-17α-methyl-Δ$^{4,9}$-estradiene-17β-ol-3-one.

28. A composition of claim 15 when the compound is selected from the group consisting of 11β-vinyl-17α-methyl-17β-acetyl-Δ$^{4,9}$-estradiene-3-one and 11β-vinyl-17β-acetoxy-17β-acetyl-Δ$^{4,9}$-estradiene-3-one.

29. A method of inducing progestomimetic activity in warm-blooded animals comprising administering to warm-blooded animals a progestomimetically effective amount of at least one compound of claim 1.

30. The method of claim 29 wherein the compound has acetoxy or ethynyl in the 17α-position and hydroxy or acetyl in the 17β-position.

31. The method of claim 29 wherein the compound is 11β-vinyl-17α-methyl-17β-acetyl-$\Delta^{4,9}$-estradiene-3-one.

32. The method of claim 29 wherein the compound is 11β-vinyl-17α-acetoxy-17β-acetyl-$\Delta^{4,9}$-estradiene-3-one.

* * * * *

UNITED STATES PATENT AND TRADEMARK OFFICE
CERTIFICATE OF CORRECTION

PATENT NO. : 4,233,296
DATED : November 11, 1980
INVENTOR(S) : Jean Georges Teutsch et al.

It is certified that error appears in the above—identified patent and that said Letters Patent is hereby corrected as shown below:

Column 7, line 27: "$8\alpha]_D^{20}$" should read -- $[\alpha]_D^{20}$ --.

Column 8, line 49: Change "ecetal" to read -- acetal --.

Column 9, line 64: Change "2 mg" to read -- 2 gm --.

Column 10, line 12: Change "ethylnyl" to read -- ethynyl --.

line 67: Change "-66$^9$" to read -- -$\Delta^9$ --.

Column 16, Table IV, FINAL PRODUCT Column line 5: "+3°" should read -- ±3° --.

line 50: "acetyl:$\Delta$" should read -- acetyl-$\Delta$ --.

Signed and Sealed this

Twenty-sixth Day of May 1981

[SEAL]

Attest:

RENE D. TEGTMEYER

Attesting Officer    Acting Commissioner of Patents and Trademarks